(12) United States Patent
Merigian

(10) Patent No.: US 12,342,993 B2
(45) Date of Patent: Jul. 1, 2025

(54) PORTABLE, FOLDABLE AND HANDHELD MULTIPURPOSE MEDICAL INSTRUMENT (OPTHALMOTOPHARYNGODERMATOSCOPE) FOR USE IN TELEMEDICINE TO EXAMINE EARS, MOUTH, EYES, SKIN, AND NASAL CAVITY AND DETECT BODY TEMPERATURE

(71) Applicant: Kevin S. Merigian, Eads, TN (US)

(72) Inventor: Kevin S. Merigian, Eads, TN (US)

( * ) Notice: Subject to any disclaimer, the term of this patent is extended or adjusted under 35 U.S.C. 154(b) by 345 days.

(21) Appl. No.: 17/854,792

(22) Filed: Jun. 30, 2022

(65) Prior Publication Data

US 2024/0000397 A1  Jan. 4, 2024

(51) Int. Cl.
| | |
|---|---|
| *A61B 1/227* | (2006.01) |
| *A61B 1/00* | (2006.01) |
| *A61B 1/233* | (2006.01) |
| *A61B 1/24* | (2006.01) |
| *A61B 5/00* | (2006.01) |

(Continued)

(52) U.S. Cl.
CPC .......... *A61B 1/227* (2013.01); *A61B 1/00052* (2013.01); *A61B 1/233* (2013.01); *A61B 1/24* (2013.01); *A61B 5/01* (2013.01); *A61B 5/441* (2013.01); *A61B 5/7465* (2013.01);

(Continued)

(58) Field of Classification Search
CPC .............................. A61B 1/227; A61B 1/2275
See application file for complete search history.

(56) References Cited

U.S. PATENT DOCUMENTS 3,812,847 A  *  5/1974  Moore ................. A61B 3/1208
                                                                362/253
5,429,119 A  *  7/1995  Griffin ................. A61B 3/1208
                                                                403/103

(Continued)

FOREIGN PATENT DOCUMENTS

| | | |
|---|---|---|
| CN | 201727493 U | 2/2011 |
| CN | 201727494 U | 2/2011 |

(Continued)

OTHER PUBLICATIONS

AMD Global Telemedicine; Verascope; https://amdtelemedicine.com/product/multi-purpose-medical-camera-and-scope-system/, Jul. 14, 2022.

(Continued)

*Primary Examiner* — Julianna N Harvey
(74) *Attorney, Agent, or Firm* — HULSEY P.C.

(57) ABSTRACT

A portable, foldable and handheld multipurpose medical instrument for use in a telemedicine application is disclosed. The medical instrument includes a first housing and a second housing placed over the first housing. The second housing includes a disposable examining tip having an image capturing unit, a temperature sensor and a light source. The medical instrument includes a plurality of buttons for operating the image capturing unit, the temperature sensor and the light source. The medical instrument includes a plurality of display screens for displaying the images, or recorded video and displaying the temperature readings during the examination of ears, eyes, nasal cavity and mouth and detection of body's temperature. In one implementation, the medical instrument transmits the data remotely to a server or a user device.

16 Claims, 7 Drawing Sheets

(51) Int. Cl.
*A61B 5/01* (2006.01)
*A61B 3/14* (2006.01)
(52) U.S. Cl.
CPC ............ *A61B 1/00016* (2013.01); *A61B 3/14* (2013.01); *A61B 5/0077* (2013.01); *A61B 2562/0271* (2013.01)

(56) References Cited

U.S. PATENT DOCUMENTS

| | | | |
|---|---|---|---|
| 6,106,457 A * | 8/2000 | Perkins | A61B 1/00105 600/172 |
| 6,319,199 B1 | 11/2001 | Sheehan et al. | |
| 10,045,683 B2 | 8/2018 | Farr et al. | |
| 10,182,710 B2 | 1/2019 | Sezan et al. | |
| 10,918,338 B2 | 2/2021 | Sayani et al. | |
| 11,013,468 B2 | 5/2021 | Mirza et al. | |
| 2003/0171655 A1* | 9/2003 | Newman | A61B 1/227 600/200 |
| 2005/0010084 A1* | 1/2005 | Tsai | A61B 1/00052 600/109 |
| 2005/0171399 A1* | 8/2005 | Rich | A61B 1/227 600/200 |
| 2010/0105988 A1* | 4/2010 | Hasbun | A61B 1/227 600/245 |
| 2010/0191063 A1 | 7/2010 | Hsu | |
| 2012/0130252 A1 | 5/2012 | Pohjanen et al. | |
| 2012/0218514 A1* | 8/2012 | Kwong | A61B 1/00105 428/397 |
| 2015/0223669 A1* | 8/2015 | Goldfain | A61B 1/00105 600/109 |
| 2015/0327775 A1 | 11/2015 | Carter | |
| 2016/0066797 A1 | 3/2016 | Lee et al. | |
| 2019/0038135 A1 | 2/2019 | Lee et al. | |
| 2020/0358925 A1 | 11/2020 | Hall | |
| 2021/0068646 A1 | 3/2021 | Zhang et al. | |

FOREIGN PATENT DOCUMENTS

| | | |
|---|---|---|
| CN | 201855254 U | 6/2011 |
| CN | 102309309 B | 9/2013 |
| CN | 102309310 B | 3/2014 |
| CN | 209391888 U | 9/2019 |
| CN | 210902919 U | 7/2020 |
| CN | 211324876 U | 8/2020 |
| CN | 213940674 U | 8/2021 |
| DE | 202011000974 U1 | 2/2012 |
| DE | 202011000975 U1 | 2/2012 |
| DE | 202016105331 U1 | 12/2016 |
| FR | 2911059 A1 | 7/2008 |
| KR | 20170038597 A | 4/2017 |
| KR | 101804094 B1 | 12/2017 |
| KR | 20190139106 A | 12/2019 |
| TW | 1403302 B | 8/2013 |
| TW | 1455702 B | 10/2014 |
| WO | 2014105649 | 7/2014 |
| WO | 2015145424 | 10/2015 |
| WO | 2021021438 | 2/2021 |

OTHER PUBLICATIONS

The Medical Futurist; Smartphone Video Otoscope To The Rescue: The HearScope Review; https://medicalfuturist.com/smartphone-video-otoscope-to-the-rescue-the-hearscope-review/, Sep. 22, 2020.

* cited by examiner

PORTABLE, FOLDABLE AND HANDHELD MULTIPURPOSE MEDICAL INSTRUMENT (OPTHALMOTOPHARYNGODERMATOSCOPE) FOR USE IN TELEMEDICINE TO EXAMINE EARS, MOUTH, EYES, SKIN, AND NASAL CAVITY AND DETECT BODY TEMPERATURE

FIELD OF THE INVENTION

The present invention generally relates to a medical instrument (opthalmotopharyngodermatoscope). More specifically, the present invention relates to a portable, foldable, and handheld multipurpose medical instrument such as an otolaryngoscope or otoscope or auriscope or otopharyngodermatoscope capable of examination of ears, mouth, eyes, and nasal cavity, skin lesions and rashes and detection of body temperature.

BACKGROUND OF THE INVENTION

It is known that medical professionals use different medical instruments for examining the ear, nasal cavity, and throat of a patient. For example, the medical professionals use otoscopes for examination of ear, nasal cavity, and throat. Further, the medical professionals use ophthalmoscopes for eye examination. Furthermore, the medical professionals use thermometers for detecting body temperature. Some of the medical instruments integrate one or more functionalities such as a display screen with other examining and diagnostic tools into a single instrument and enhance the usability of such medical instrument(s).

Several such devices have been disclosed in the past. One such example is disclosed in a United States Publication No. 20160066797, entitled "TR309—Portable Otoscope Video Viewer" ("the '797 Publication"). The '797 Publication discloses that TR 309 is a portable otoscope video adaptor and viewing unit, designed to make the examination of ears, nose, throat, and eyes more easily attainable and to increase the size of the obtained view. It contains a built-in Camera/LCD/video recorder/otic thermometer in a handheld unit which fits the Welch Allyn or Heine otoscope or works totally independently. It is designed to fit into any shirt pocket for portability. It also can be easily pushed to the side, allowing the normal use of the Welch Allyn or Heine otoscope, or the 309's otic adapter, allowing foreign body removal or tympanocentesis. The TR 309 also provides for an unobstructed view and access to the eardrum, nose, throat, or eye for surgery while under real time view on the unit's LCD. A new ear specula and needle specifically designed for tympanocentesis is also described.

Another example is disclosed in a United States Publication No. 20120130252, entitled "Producing an Image" ("the '252 Publication"). The '252 Publication discloses an optical component that is connectable to a camera unit and comprises a data structure including data associated with the optical component. When the optical component is connected to the camera unit, data associated with the optical component is transferred to the camera unit. Image production of an organ by the camera unit is controlled based on the data associated with the optical component.

Another example is disclosed in a PCT Publication No. 2021021438, entitled "Diagnostic Tool-Based Health Management System" ("the '438 Publication"). The '438 Publication discloses a point-of-care system with a diagnostic tool and a base station with a display and in communication with the diagnostic tool is described. Used in diagnosing health conditions for a tissue under analysis, the diagnostic tool includes a handle and a head portion. The head portion includes a speculum and optical spectroscopy (OS) data acquisition components positioned within the head portion. The OS data acquisition components are configured to (i) emit light toward the tissue under analysis, (ii) receive light reflected at least in part from the tissue under analysis based on the emitted light, and (iii) determine reflectance spectra associated with the received light. Either the diagnostic tool or a base station includes analytic components configured to (i) generate diagnostic metrics including characteristics of the reflectance spectra and (ii) compare these characteristics to data associated with characteristics of known reflectance spectra associated with healthy and/or unhealthy tissue of patients.

Although the above disclosures are useful, they have few disadvantages. For example, some of the medical instruments have inadequate lighting, and cannot capture and review images or data in real time on an external device or on the instrument itself. Further, some of the medical instruments are expensive and difficult to maintain. In addition, the current healthcare system has been slow to embrace patient-centered care. Hospitals and clinics have created sterile and inhospitable atmospheres for patient diagnosis and care. Further, it takes considerable time to examine patient's ears, mouth, and nasal cavity and detect his/her body temperature. Furthermore, some of the known devices cannot be used by the healthcare professionals due to the conditions at the hospitals and clinics since the Coronavirus (Covid-19) pandemic.

Therefore, there is a need for a medical instrument that is portable, and allows to operate using hand and allows to visually assess the ear canals, tympanic membranes with a temperature measurement, visualize oral cavity, tonsils and pharynx in patients at the patient's home or work office.

BRIEF SUMMARY OF THE INVENTION

It is an object of the present invention to provide a medical instrument for use in a telemedicine application that avoids the drawback of known otoscopes.

It is another object of the present invention to provide a cost-effective, lightweight, portable, foldable and handheld multipurpose medical instrument for use in a telemedicine application.

It is another object of the present invention to provide a medical instrument that provides simultaneous viewing the collected information in real time or for later viewing and transmission of the obtained information to a server or a user device.

To overcome the limitations here stated, the present invention provides a portable, foldable, and handheld multipurpose medical instrument for use in a telemedicine application. The medical instrument includes a first housing, and a second housing placed over the first housing. The second housing includes a disposable examining tip having an image capturing unit, a temperature sensor, and a light source. The medical instrument includes a plurality of buttons for operating the image capturing unit, the temperature sensor, and the light source. The medical instrument includes a plurality of display screens for displaying the images, or recorded video and displaying the temperature readings during the examination of external ear canal, tympanic membrane, oral-pharyngeal cavity, retina of the eyes, skin lesions and rashes, and detection of body's temperature.

In one advantageous feature of the present invention, the first housing folds over the second housing enclosing the disposable examining tip. As a result, the medical instrument becomes portable and protects the disposable examining tip having the image capturing unit, the temperature sensor, and the light source when not in use.

In another advantageous feature of the present invention, the medical instrument transmits the data remotely to a server or a user device as it is being recorded for analysing, storing, and reporting on the collected data.

In another advantageous feature of the present invention, the medical instrument provides an improved handheld multipurpose medical instrument that helps to conduct multiple diagnostic procedures and examination of a patient's ears, or other orifices or body members, eyes, body temperature, and of capturing that information during examination while using a single device.

In yet another advantageous feature of the present invention, the medical instrument allows to operate it using hand and allows to visually assess the ear canals, tympanic membranes with a temperature measurement, visualize oral cavity, tonsils, pharynx, eyes and skin lesions in patients at the patient's home or work office.

Yet another advantageous feature of the present invention, the medical instrument operates as an otolaryngoscope or otoscope or auriscope or opthalmotopharyngodermatoscope capable of examination of eyes, ears, mouth, and nasal cavity and detection of body temperature.

Features and advantages of the invention hereof will become more apparent considering the following detailed description of selected embodiments, as illustrated in the accompanying FIGUREs. As will be realized, the invention disclosed is capable of modifications in various respects, all without departing from the scope of the invention. Accordingly, the drawings and the description are to be regarded as illustrative in nature.

BRIEF DESCRIPTION OF THE DRAWINGS

The present invention will now be described in detail with reference to the drawings, which are provided as illustrative examples of the invention as to enable those skilled in the art to practice the invention. It will be noted that throughout the appended drawings, like features are identified by like reference numerals. Notably, the FIGUREs and examples are not meant to limit the scope of the present invention to a single embodiment, but other embodiments are possible by way of interchange of some or all of the described or illustrated elements and, further, wherein.

DETAILED DESCRIPTION OF THE EMBODIMENTS

The detailed description set forth below in connection with the appended drawings is intended as a description of exemplary embodiments in which the presently disclosed invention may be practiced. The term "exemplary" used throughout this description means "serving as an example, instance, or illustration," and should not necessarily be construed as preferred or advantageous over other embodiments. The detailed description includes specific details for providing a thorough understanding of the presently disclosed medical instrument. However, it will be apparent to those skilled in the art that the presently disclosed invention may be practiced without these specific details. In some instances, well-known structures and devices are shown in functional or conceptual diagram form in order to avoid obscuring the concepts of the presently disclosed medical instrument.

In the present specification, an embodiment showing a singular component should not be considered limiting. Rather, the invention preferably encompasses other embodiments including a plurality of the same component, and vice-versa, unless explicitly stated otherwise herein. Moreover, the applicant does not intend for any term in the specification to be ascribed an uncommon or special meaning unless explicitly set forth as such. Further, the present invention encompasses present and future known equivalents to the known components referred to herein by way of illustration.

Although the present disclosure provides a description of a medical instrument for use in a telemedicine application, it is to be further understood that numerous changes may arise in the details of the embodiments of the medical instrument. It is contemplated that all such changes and additional embodiments are within the spirit and true scope of this disclosure.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure.

Figure 1:
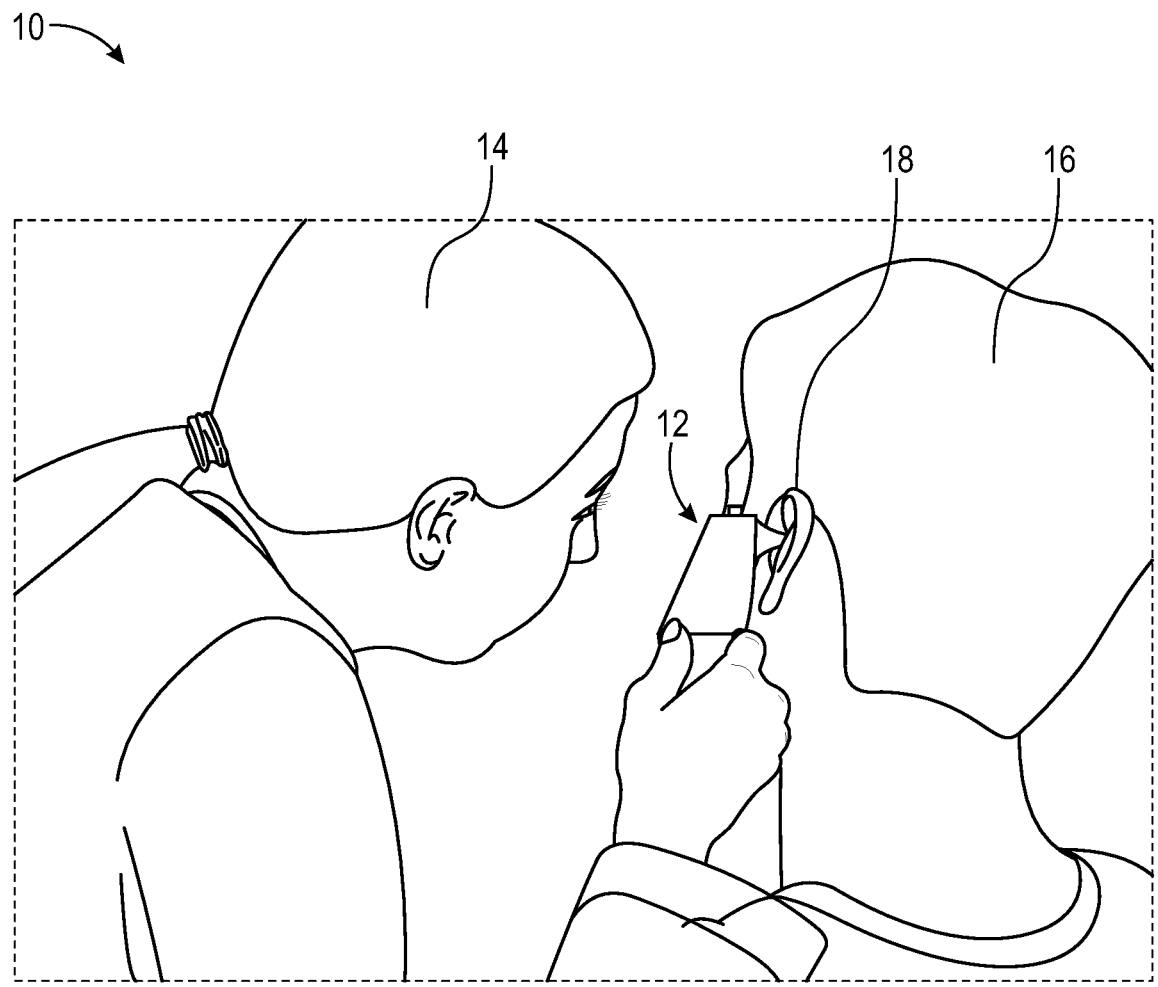
FIG. 1 illustrates an environment of a medical instrument used by a healthcare professional on a living subject such as an animal or human body for examination of ear, in accordance with one exemplary embodiment of the present invention.
Figure 2C:
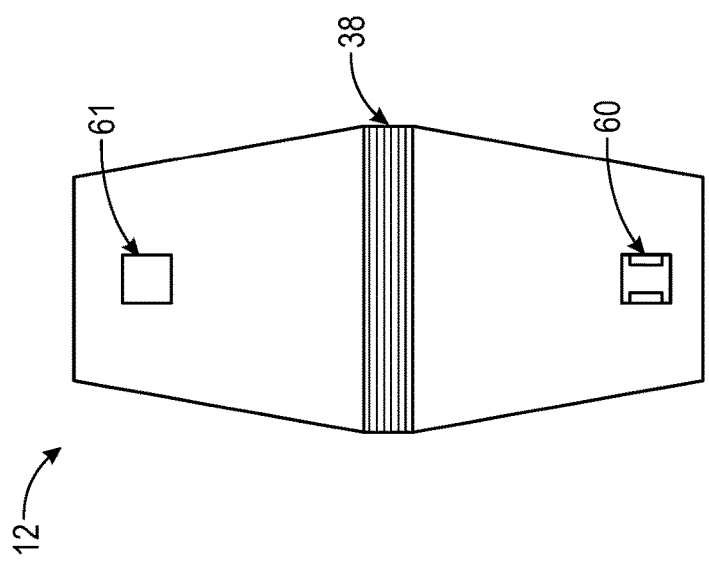
FIGS. 2A, 2B, 2C, 2D and 2E illustrate a side view, a top view, a bottom view in folded state, a front view and a rear view, respectively of a medical instrument, in accordance with one embodiment of the present invention.
Figure 2B:
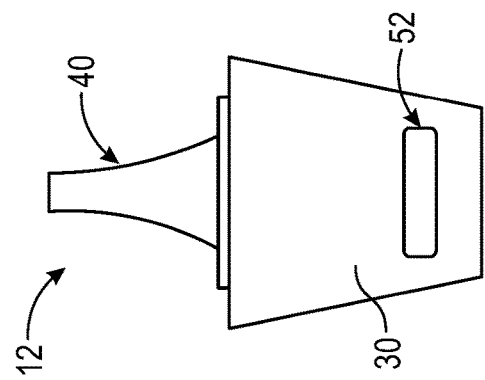
Figure 2A:
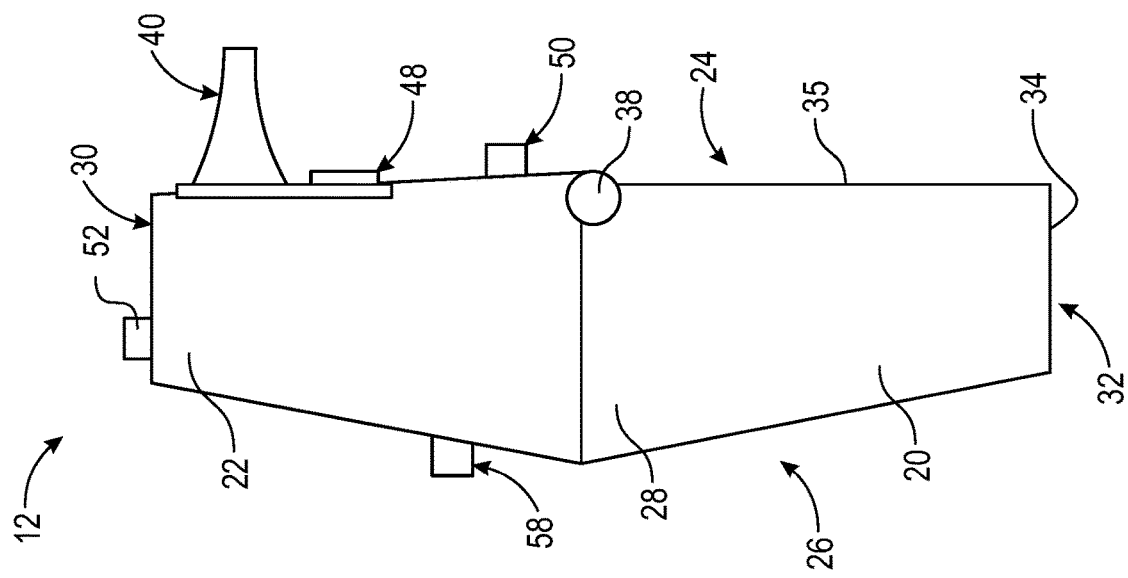
Figure 2E:
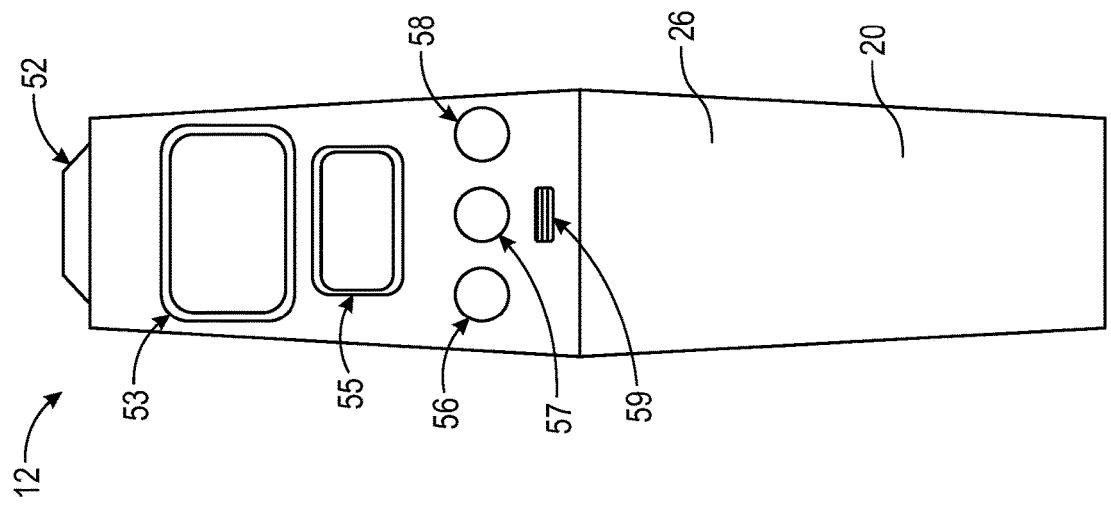
Figure 2D:
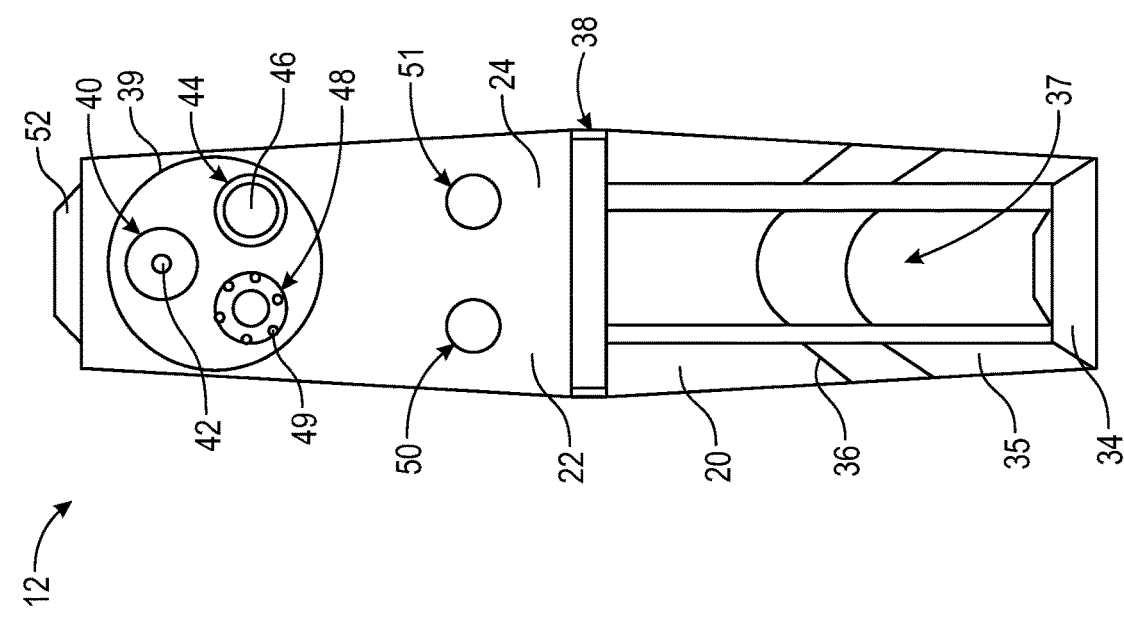

In one embodiment, the present invention discloses a portable, foldable and handheld multipurpose medical instrument such as an otolaryngoscope or otoscope or auriscope capable of examination of ears, mouth, and nasal cavity and detection of body temperature. FIG. 1 shows an environment 10 of medical instrument 12 used by healthcare professional 14 on patient 16 to examine his/her ear 18, in accordance with one exemplary embodiment of the present invention. In the present invention, medical instrument 12 operates as an electronic or digital otolaryngoscope or otoscope or auriscope for examination of ears, mouth, and nasal cavity and detection of body temperature of patient 16 at their homes or work office. Although it is shown that healthcare professional 14 is examining patient's ear in FIG. 1, it is obvious to a person skilled in the art that patient 16 himself/herself or with the help of a caretaker or family member can operate medical instrument 12 for examination of ears, mouth, and nasal cavity and detection of body temperature without departing from the scope of the present invention.

Now referring to FIGS. 2A, 2B, 2C, 2D and 2E, a side view, a top view, a bottom view in folded state, a front view and a rear view, respectively of medical instrument 12, in accordance with one embodiment of the present invention. Medical instrument 12 includes a first housing 20 and a second housing 22. First housing 20 indicates a bottom housing and second housing 22 positions above first housing 20 (as top housing 20). Medical instrument 12 has front end 24, rear end 26, sides 28, top side 30, and a bottom side 32. First housing 20 encompasses a base 34 having walls 35. Walls 35 extend from base 35 and includes support structures 36 at its length to provide required strength to first housing 20. Walls 35 position at three sides forming an opening 37 at front end 24, as shown in at least FIG. 2D.

Figure 3:
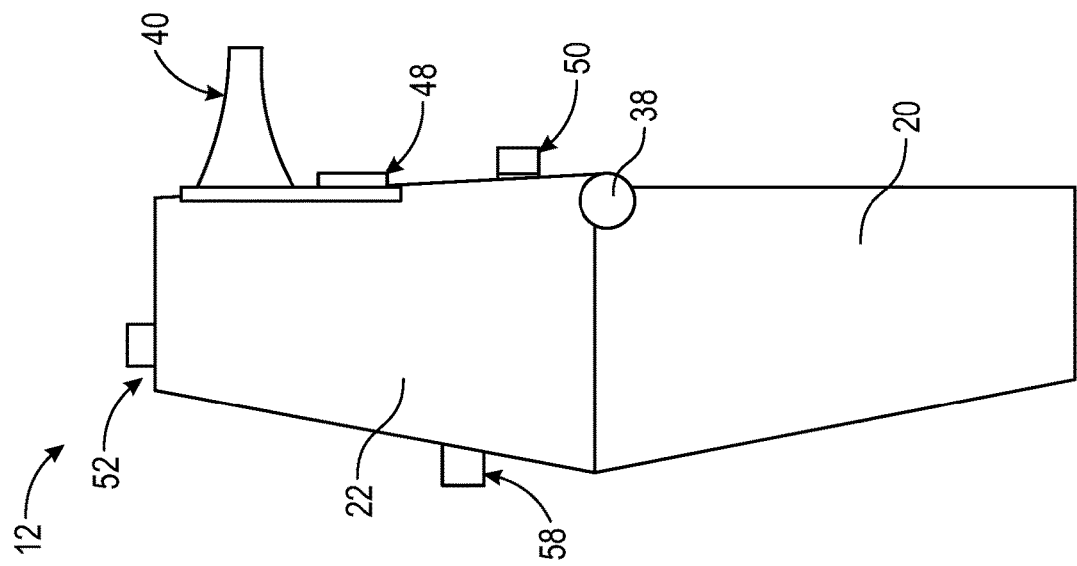

Medical instrument 12 includes a hinge 38. Hinge 38 positions at front end 24 and connects first housing 20 and second housing 22 at their distal ends. Hinge 38 helps to fold first housing 20 over second housing 304, as shown in FIG. 3, for example. Further, second housing 22 includes extended section 39. Extended section 39 receives examining tip 40 such as an ear spectrum. First image capturing unit 42 captures images and/or video when examining tip 40 is inserted into ear canal, nasal cavity or mouth during the examination of ears, nasal cavity or mouth, respectively depending on the diagnosis needed. Extended section 39 receives dermatologic lens 44 and second image capturing unit 46. Dermatologic lens 44 and second image capturing unit 46 capture images of skin with increased clarity of focus, detail and depth. Second image capturing unit 46 is able to manipulate captured images (e.g., applying filters, noise reduction, changing colour tones and contrasts etc.) to produce final images. Further, extended section 39 receives third image capturing unit 48. Third image capturing unit 48 includes light sources 49. Light sources 49 help to project light into mouth, throat or eyes and third image capturing unit 48 captures images and/or video during the examination of oral cavity and/or throat depending on the diagnosis needed. Further, second housing 22 includes power ON/OFF button 50 and light source button 51. Light source button 51 helps to control intensity of light produced by light sources 49.

At top side 30, second housing 22 encompasses focus button 52. Focus button 52 helps to adjust focus i.e., focal length of lens or adjust the lighting by light sources 49. In other words, pressing focus button 52 adjusts the focal length or magnification of lens in image capturing units 42, 46 and 48 during the examination of ears, eyes, nasal cavity, mouth, etc.

Further, second housing 22 encompasses first display 53 and second display 55. First display 53 displays image/video captured by first image capturing unit 42. Second display 55 displays image/video captured by second and third image capturing units 46, 48. Further, second housing 22 encompasses menu button 56, record button 57 and image capturing unit button 58. Menu button 56 helps to select desired option to configure the medical instrument 12. Record button 57 helps to record and store the images/video in a memory (not shown). Image capturing unit button 58 helps to operate image capturing units 42, 46 and 48. Additionally, second housing 22 encompasses a port 59 such as a Universal Serial Bus (USB) port or charging port for charging the electrical components of medical instrument 12 or transferring the data to and from medical instrument 12 to other devices such as a server (not shown), for example.

Figure 4:
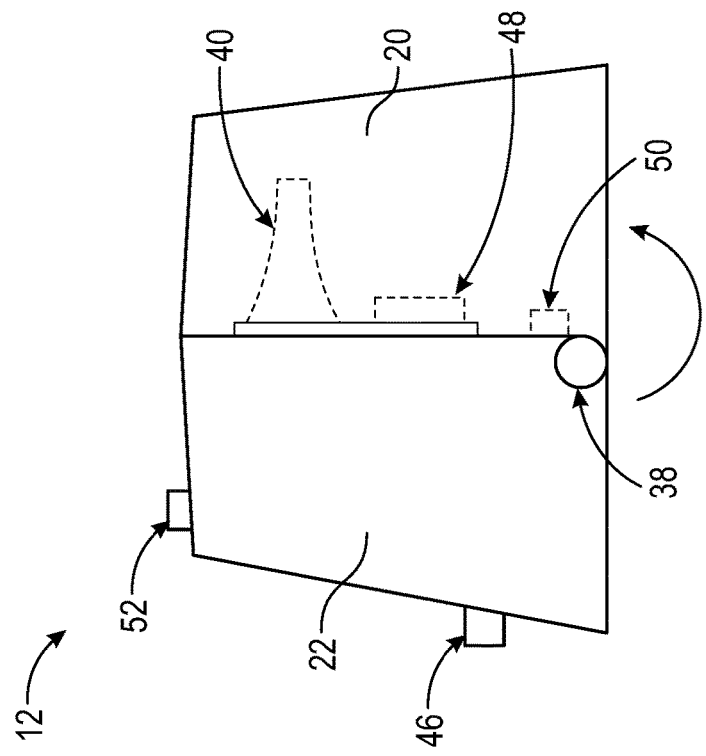
FIGS. 3 and 4 illustrate operational views of the medical instrument, in accordance with one embodiment of the present invention.

FIGS. 3 and 4 show medical instrument 12 in operational state and folded state, respectively. Medical instrument 12 includes a male member (or clasp) 60 and a female member (or hole) 61. Male member 60 and female member 61 indicate a male latch and a female latch, respectively. In one example, male member 60 positions at first housing 20 and female member 61 positions at second housing 304, or vice versa. In the operational state, male member 60 and female member 61 connect to lock the position of first housing 20 and second housing 22, as shown in FIG. 4. As specified above, first housing 20 includes opening 37 and hinge 38. When not in use, first housing 20 folds via hinge 38 over second housing 22 such that examining tip 40, dermatologic lens 44 and other components at front end 24 of second housing 22 are housed or received in opening 37 of first housing 20, as shown in FIG. 4. Folding of first housing 20 over second housing 22 saves space and presents easy transport.

Figure 5:
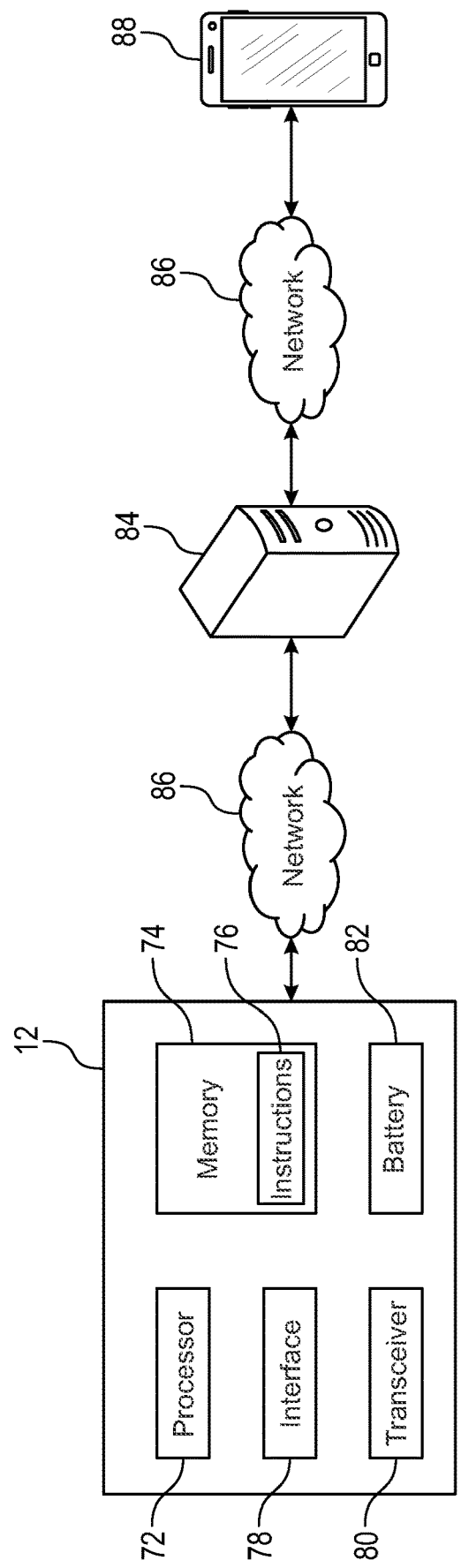
FIG. 5 shows the medical instrument communicatively connected to a server and a user device, in accordance with one embodiment of the present invention.

Now referring to FIG. 5, a block diagram of medical instrument 12 is shown, in accordance with one embodiment of the present invention. Medical instrument 12 encompasses processor 72, and memory 74. Processor 72 includes a central processing unit (CPU), a graphics processing unit (GPU) or both. In one example, memory 74 includes instructions 76 stored therein. Instructions 76 may also reside, completely or at least partially, within the memory 74 and/or within the processor 72 during execution thereof. Instructions 76 may further be transmitted or received over a network 86 via transceiver 80 utilizing any one of several well-known transfer protocols.

Medical instrument 12 encompasses interface 78 such as hardware and/or software devices/applications used for operating medical instrument 12. Medical instrument 12 encompasses transceiver 80 for sending or receiving instructions/data from other devices such as server 84 or user device 88. Medical instrument 12 further encompasses battery 82 for powering electronic components in medical instrument 12.

Medical instrument 12 operates as a standalone device and/or communicatively connects to other devices such as server 84 or user device 88 via network 86. Here, server 84 indicates a central server operated by a hospital, medical institution, etc., for storing and processing the health data of patient(s) 16. User device 88 indicates a device such as a mobile phone, tablet, laptop, smartwatch, desktop, etc. used by patient 16, healthcare professional 14, or any other individual(s). Network 86 includes a wireless network, a wired network, or a combination thereof. Network 86 can be implemented as one of the different types of networks, such as intranet, local area network (LAN), wide area network (WAN), the internet, and the like. The network 86 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 86 may include a variety of network devices, including routers, bridges, servers, computing devices, storage devices, and the like.

In operation, healthcare professional 14 places disposable examining tip 40 into ear canal, nasal cavity, or mouth during the examination of ears, nasal cavity or mouth, respectively depending on the diagnosis needed. Here, healthcare professional 14 engages one of the buttons to illuminate light source 49 and captures images or records video using image capturing unit 42 during the examination of ears, nasal cavity and/or mouth. In one example, the images captured, or video being recorded are displayed at first display screen 53. In one example, medical instrument 12 records the images at intervals of 15, 30, 45, 60, 90, 120 seconds. Alternatively, medical instrument 12 captures the images or records the video and displays on first display screen 53 in real-time.

Optionally, medical instrument 12 employs a temperature sensor (not shown) to capture patient's body temperature and displays the temperature readings on second display screen 55.

In one implementation, medical instrument 12 stores the images and video of the ears, nasal cavity and/or mouth and the temperature readings captured during their examination in memory 74. In another implementation, medical instrument 12 transmits the data (i.e., images and video of the ears, nasal cavity and/or mouth and the temperature readings) in real-time to server 84 and/or user device(s) 88. Healthcare professionals 14, patient 16 or any other interested persons view the data captured and recorded by medical instrument 12.

Figure 6:
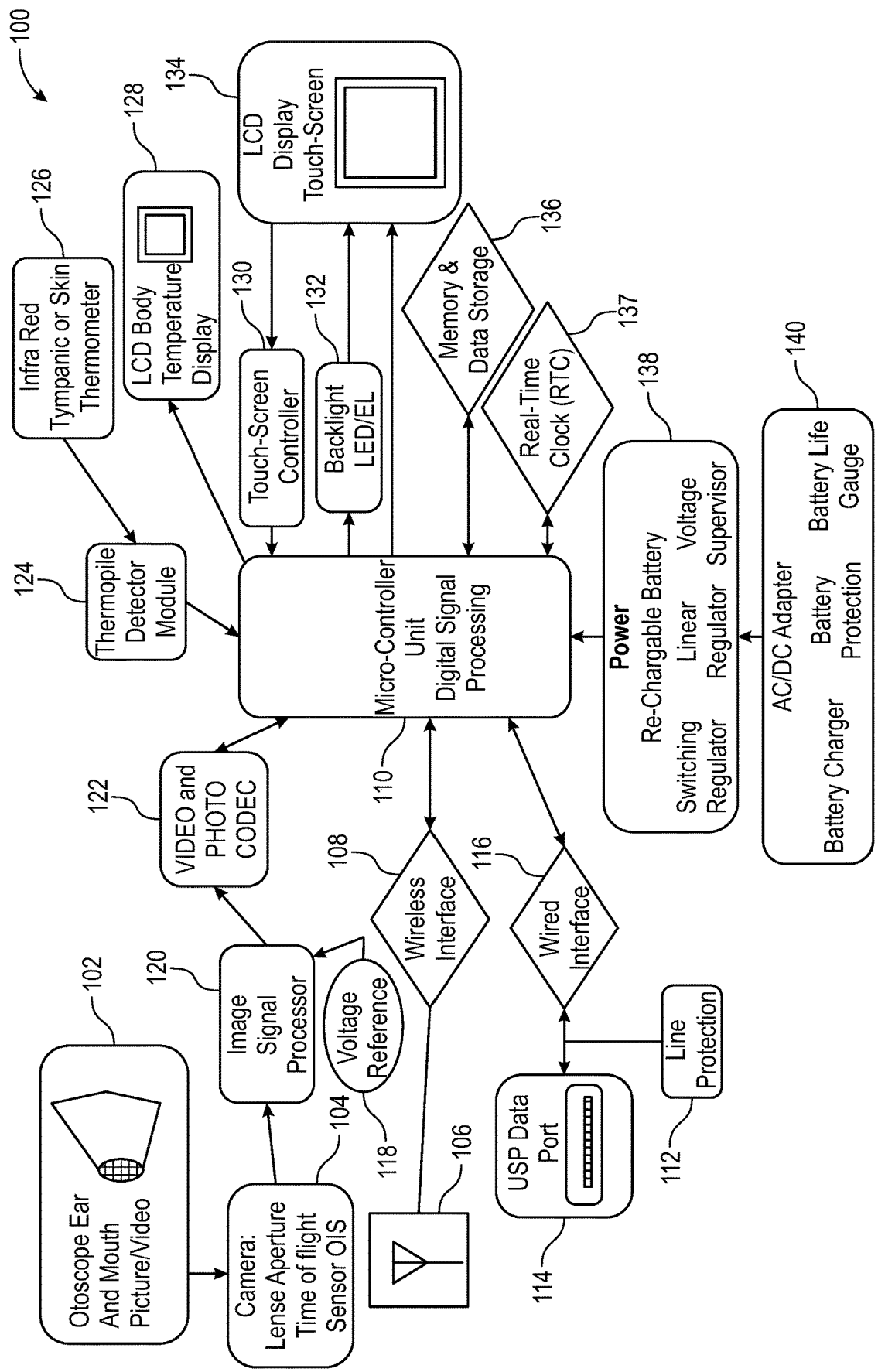
FIG. 6 shows an internal design on a medical instrument, in accordance with one exemplary embodiment of the present invention.

FIG. 6 shows an internal design on medical instrument 100, in accordance with one exemplary embodiment of the present invention. The Medical instrument 100 implements and operates similar to medical instrument 12, as explained above. The three ameras 104 capture ear, eye, skin and/or mouth pictures or videos (102). Medical instrument 100 includes wireless communication module 106 connected to microcontroller 110 via wireless interface 108. In one implementation, medical instrument 100 encompasses line protection circuit 112 for protecting the electrical components from electric fluctuations. In addition, medical instrument 200 includes first port 114 such as a Universal Serial Bus (USB) port or charging port for charging the electrical components of medical instrument 100 via wired interface 116.

In accordance with the present embodiment, The three cameras 104 capture the images and utilizes image signal processor 120 to enhance the image using voltage reference 118. Image signal processor 120 provides the image to video and photo codec 122 for encoding the image. Further, thermopile detector module 124 supplies infrared tympanic or skin thermometer readings to microcontroller 110. Microcontroller 110 processes the image and temperature readings. In one example, microcontroller 210 displays the temperature readings on LCD body temperature display 128. Further, microcontroller 110 controls and displays information on display screen 134 using touchscreen controller 130 and backlight LED/EL 132. Display screen 134 configures to display the images captured by camera 104.

In addition, medical instrument 100 encompasses memory 136 for storing the images captured by the three cameras 104 and temperature captured by thermometer 126. Microcontroller 110 controls real-time clock 137 of medical instrument 100. Medical instrument 100 receives power from a rechargeable battery 138 via AC/DC adapter 140.

Figure 7:
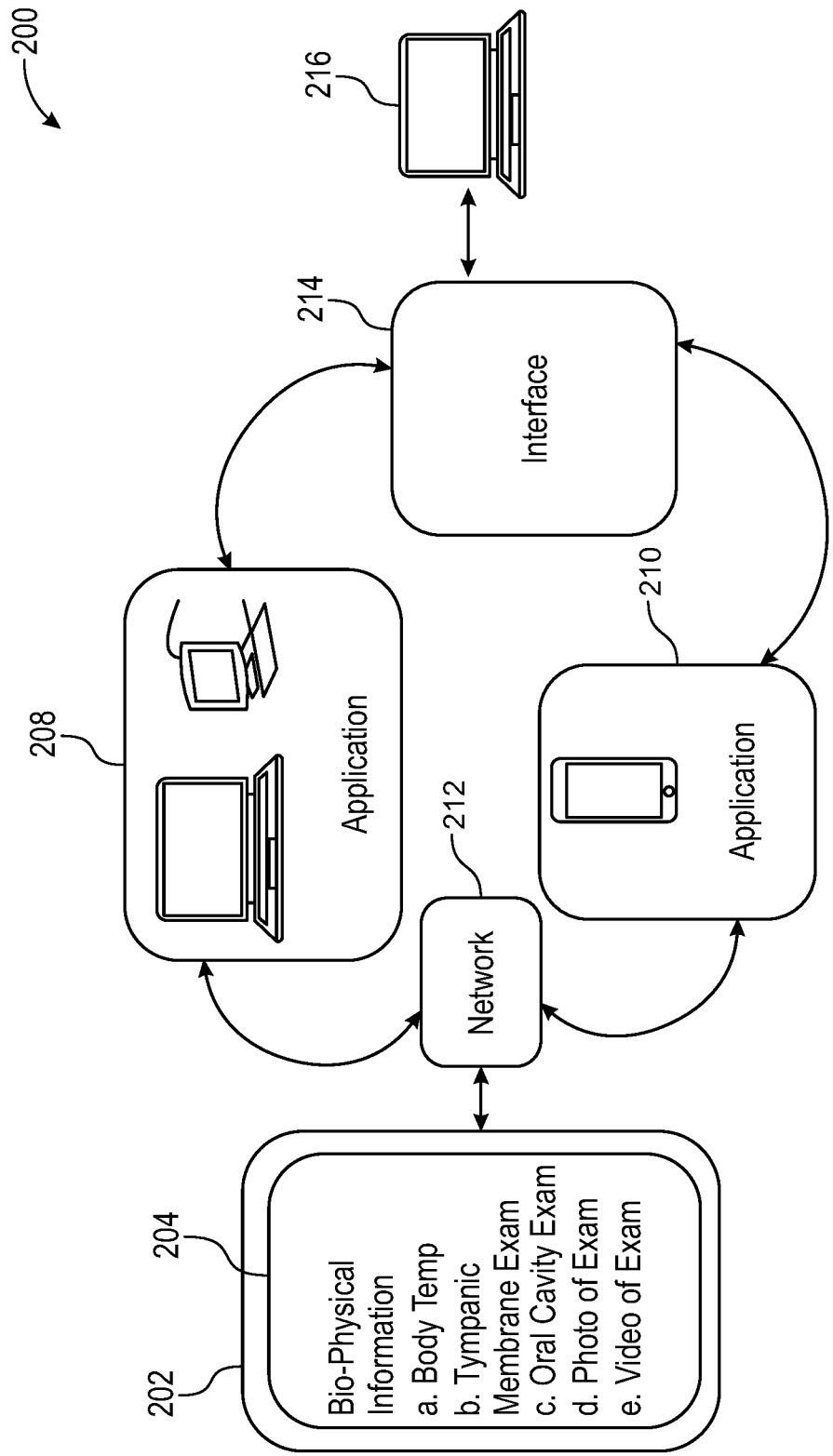
FIG. 7 shows a network architecture of a medical instrument communicating with a server operated/managed by a telemedicine provider/hospital/government/third party telehealth service provider, in accordance with one exemplary embodiment of the present invention.

FIG. 7 shows a network architecture 200 of medical instrument 202 communicating with server 216 operated/managed by a telemedicine provider/hospital/government/third party telehealth service provider. Here, medical instrument 202 includes data or bio-physical information 204 of a user (not shown) such as ECG, heart sounds, breath sounds, bruits, lung sounds, etc. Medical instrument 202 communicatively connects to user devices 208, 210 such as mobile devices, laptops, etc. via network 212. In one example, each of user devices 208, 210 includes a software application specifically configured to interact with medical instrument 202 and server 216. In one example, user devices 208, 210 utilize an interface 214 specifically interact with server 216 via network 212. Network 212 includes, but not limited to, Bluetooth, internet, Wi-Fi, Li-Fi, wired network.

Medical instrument 12 communicates with a server (similar to server 216). Healthcare professionals can access the data remotely and provide required diagnosis and/or care.

The presently disclosed medical instrument 12, 100, or 202 operates with third party applications/software such as On-call Health™, Nextgen Virtual Visits™, Mend™, WebPT™, SimplePractice™, Modernizing Medicine™, Therapy Notes™, Updox™, Vivadox™, Kareo Billing™, Zoom™, Webex™ and any other service providers for telehealth or telemedicine applications.

The presently disclosed medical instrument integrates with other medical devices and help to provide telemedicine to patients. The medical instrument captures and streams/transmits the images of ears, eyes, nasal cavity and/or mouth and skin lesions to medical practitioners. Further, the medical instrument presents a dashboard with options to integrate and match workflow of an in-person visit in a virtual/online world. For instance, an on-site medical practitioner captures vitals of the patient, prepares intake material or information and submits to the remote service provider/healthcare professional. The remote service provider/healthcare professional securely accesses the information, and reviews the information before consulting the patient. This helps the remote service provider/healthcare professional to have full information about the patient. The medical instrument helps to provide the required consultation to the patients at a relatively low cost.

The medical instrument has applications in academic/education setting, addiction treatment, community health centers, correctional facilities, hospitals/health systems, physician services, retail/pharmacy, school-based clinics, skilled nursing facilities, urgent care, emergency medical systems, etc.

A person skilled in the art appreciates that the medical instrument may come in a variety of shapes and sizes depending on the need and comfort of the user. Further, many changes in the design and placement of components may take place without deviating from the scope of the presently disclosed medical instrument.

In the above description, numerous specific details are set forth such as examples of some embodiments, specific components, devices, methods, in order to provide a thorough understanding of embodiments of the present disclosure. It will be apparent to a person of ordinary skill in the art that these specific details need not be employed, and should not be construed to limit the scope of the disclosure.

In the development of any actual implementation, numerous implementation-specific decisions must be made to achieve the developer's specific goals, such as compliance with system-related and business-related constraints. Such a development effort might be complex and time-consuming, but may nevertheless be a routine undertaking of design, fabrication, and manufacture for those of ordinary skill. Hence as various changes could be made in the above constructions without departing from the scope of the invention, it is intended that all matter contained in the above description or shown in the accompanying drawings shall be interpreted as illustrative and not in a limiting sense.

The foregoing description of embodiments is provided to enable any person skilled in the art to make and use the invention. Various modifications to these embodiments will be readily apparent to those skilled in the art, and the novel principles and invention disclosed herein may be applied to other embodiments without the use of the innovative faculty. It is contemplated that additional embodiments are within the spirit and true scope of the disclosed invention.

What is claimed is:

1. A medical instrument, comprising:
   a first housing, comprising:
      a base; and
      walls extending from said base, wherein said walls extend from three sides and form an opening at one side;
   a second housing, comprising:
      an examining tip extending outwardly from said second housing
      a first image capturing unit positioned outside of said second housing and adjacent to said examining tip; and
      a display screen; and
   a hinge connecting said first housing and said second housing,
      wherein said examining tip inserts in one of ears, nasal cavity, and mouth of a patient, wherein said first image capturing unit captures images or records video during the examination of the ears, nasal cavity, and mouth, wherein said display screen displays the images or the video captured by said first image capturing unit, wherein said second housing positions above said first housing, wherein said first housing folds over said second housing via said hinge such that said examining tip extending outwardly from said second housing and said first image capturing unit position in said opening of said first housing, and wherein said examining tip remains extending outwardly from said second housing when said first housing folds over said second housing.

2. The medical instrument of claim 1, wherein said examining tip is disposable and removably connects to said second housing.

3. The medical instrument of claim 1, wherein said examining tip comprises a temperature sensor, and wherein said temperature sensor obtains body temperature of the patient.

4. The medical instrument of claim 1, wherein said examining tip comprises a light source at its distal end, and wherein said light source illuminates at the target of interest during the examination of the ears, eyes, nares and mouth.

5. The medical instrument of claim 1, further comprises a transceiver, wherein said transceiver transmits the images or video captured by said first image capturing unit to a server for providing remote diagnosis and care.

6. The medical instrument of claim 1, wherein said first housing comprises a male member and said second housing comprises a female member, and wherein said male member connects to said female member to position and connect said second housing over said first housing.

7. The medical instrument of claim 1, further comprises a second image capturing unit, wherein said second image capturing unit captures images of eyes and oropharynx with increased clarity of focus, detail and depth.

8. The medical instrument of claim 1, further comprises a third image capturing unit, wherein said the third image capturing unit captures images of the skin with increased clarity of focus, detail and depth.

9. The medical instrument of claim 1, wherein said second housing comprises a focus button, and wherein said focus button adjusts the focal length of said first image capturing unit during the examination of the ears, nasal cavity, and mouth.

10. The medical instrument of claim 1, wherein said examining tip comprises an ear speculum, and wherein said ear speculum inserts into the ear canal of the patient during the examination of the ear.

11. The medical instrument of claim 10, wherein said examining tip comprises a temperature sensor, and wherein said temperature sensor obtains body temperature of the patient.

12. The medical instrument of claim 10, wherein said examining tip comprises a light source at its distal end, and wherein said light source illuminates at the target of interest during the examination of the ears, nasal cavity and mouth.

13. The medical instrument of claim 10, further comprises a transceiver, wherein said transceiver transmits the images or video captured by said first image capturing unit to a server for providing remote diagnosis and care.

14. The medical instrument of claim 10, wherein said first housing comprises a male member and said second housing comprises a female member, and wherein said male member connects to said female member to position and connect said second housing over said first housing.

15. The medical instrument of claim 10, wherein said second housing comprises a focus button, and wherein said focus button adjusts the focal length of said first image capturing unit during the examination of the ears, nasal cavity, and mouth.

16. A medical instrument, comprising:
   a first housing, comprising:
      a base; and
      walls extending from said base, wherein said walls extend from three sides and form an opening at one side;
   a second housing, comprising:
      an examining tip extending outwardly from said second housing, wherein said examining tip removably connects to said second housing and is disposable, wherein said examining tip comprises a first image capturing unit; and
      a display screen, said display screen positions at the opposite side of said examining tip; and
   a hinge connecting said first housing and said second housing,
      wherein said examining tip inserts in one of ears, nasal cavity, and mouth of a patient, wherein said first image capturing unit captures images or records video during the examination of the ears, nasal cavity, and mouth, wherein said display screen displays the images or the video captured by said first image capturing unit, wherein said second housing positions above said first housing, wherein said first housing folds over said second housing via said hinge such that said examining tip extending outwardly from said second housing and said first image capturing unit position in said opening of said first housing, and wherein said examining tip remains extending outwardly from said second housing when said first housing folds over said second housing.

* * * * *